(12) United States Patent
ElSohly et al.

(10) Patent No.: US 6,790,863 B2
(45) Date of Patent: Sep. 14, 2004

(54) DIHYDROARTEMISININ AND DIHYDROARTEMISITENE DIMERS AS ANTI-CANCER AND ANTI-INFECTIVE AGENTS

(75) Inventors: Mahmoud A. ElSohly, Oxford, MS (US); Samir A. Ross, Oxford, MS (US); Ahmed M. Galal, Nasr (EG)

(73) Assignee: University of Mississippi, University, MS (US)

(*) Notice: Subject to any disclaimer, the term of this patent is extended or adjusted under 35 U.S.C. 154(b) by 0 days.

(21) Appl. No.: 10/271,960

(22) Filed: Oct. 15, 2002

(65) Prior Publication Data

US 2004/0072896 A1 Apr. 15, 2004

(51) Int. Cl.[7] .................... A61K 31/357; C07D 493/12
(52) U.S. Cl. .................. 514/450; 549/348; 549/358
(58) Field of Search .................. 514/450, 453; 549/348, 358

(56) References Cited

U.S. PATENT DOCUMENTS

| | | | |
|---|---|---|---|
| 4,952,603 A | | 8/1990 | El-Feraly et al. |
| 5,677,468 A | | 10/1997 | Zhang et al. |
| 5,856,351 A | * | 1/1999 | Zheng et al. ............... 514/450 |

OTHER PUBLICATIONS

American Cancer Society, Statistic for 2001. (http://www.cancer.org/downloads/STT/F&F2001.pdft).

Cragg, G.M., Newman, D.J., Snader, K.M.: Natural products in drug discovery and development. J. Nat. Prod., 60:52–60 (1997).

Shu Y.Z.: Recent natural products based drug development: a pharmaceutical industry perspective. J. Nat. Prod., 61:1053–1071 (1998).

Cragg, G.M., Newman, D.J., Weiss, R.B.; Coral reefs, forests, and thermal vents: the worldwide exploration of nature for novel antitumor agents. Seminar Oncol 24:156–163 (1997).

Clark, AM.: Natural products as a resource for new drugs. Pharmaceut Res. 13:1133–1141 (1996).

Report of the Coordinating Group for Research on the Structure of Qing Hao Su. K'O Hsueh T'Ung Pao 22, 142 (1977); Chem. Abstr. 87, 98788g (1977).

Beekman, A.C., Barensten, A.R.W., Woerdengag, H.J., Van Uden, W., Pras, N., ElFeraly, F.S., and Galat, A.M.; J. Nat.Prod., 60: 325 (1997).

Zheng, G.Q,; Cytotoxic terpenoids an dflavonoids from Artemisia annua, Planta Medica, 60 (1):54–7 (1994).

Woerdenbag, H.J., Moskal, T.A., Pras, N., Malingre, T.M., Kampinga, H.M., Konings, A.W.T., and El–Feraly, F.S., Cytotoxicity of artemisinin–related endoperoxides to Ehrlich ascites tumor cells, J. Nat. Prod., 56: 84a (1993).

Beekman, A.C., Woprdenberg, H.J., Kampigna, H.H., and Konings, A.W.T.; Stereochemistry–dependent cytotoxicity of some artemisinin derivatives, Phytother. Res., 10, 140 (1996).

Posner, G.H., et al; Trioxane Dimers Have Potent Anti–malarial, Anti–proliferative, and Anti–tumor Activities In Vitro, Bioorganic and Med Chem., 5:1257–65 (1997).

Posner, G.H., Ploypradith, P., Parker, M.H., O'Dowd, H., Woo, S.–H., Northdrop, J., Krasavin, M., Dolan, P., Kensler, T.W., Xie, S., and Shapiro, T.A.; Antimalarial, Anti–proliferative, and Anti–tumor Activities of Artemisin in–Derived, Chemically Robust, Trioxane Dimers, J. Med Chem., 42, 4275–80 (1999).

ElSohly, H.N., Croom, E.M., El–Feraly, F.S., and El–Sheri, M.M., J. Nat. Prod., 53(6): 1560–4 (1990).

Lin, A.J., Klyman, D.L., and Milhous, W.K., J. Med. Chem. 30, 2147 (1987).

El–Feraly, F.S., and Hufford, C.D., J. Org. Chem., 47, 1527 (1982).

El–Feraly, F.S., Ayalp, A., Al–Yahya, M.A., McPhail, D.R. and McPhail, A.T., J. Nat. Prod. 53 (1), 66–71 (1990).

\* cited by examiner

*Primary Examiner*—Charanjit S. Aulakh
(74) *Attorney, Agent, or Firm*—Greenberg Traurig LLP; Eugene C. Rzucidlo

(57) ABSTRACT

This invention comprises compositions containing dihydroartemisinin and dihydroartemisitene dimers with activity as anticancer agents and anti-protozal, including antimalarial and anti-leishmanial properties. This invention also describes methods of preparation of these compositions and methods of use of such compositions for the treatment of cancer, and protozoal infections, including malaria, or leishmaniasis. The compounds of this invention represent a potential new class of anti-tumor agents, one that has shown promising activity against solid tumors, and with a pattern of selectivity that suggests a possible new mechanism of action.

4 Claims, 11 Drawing Sheets

Fig. 1
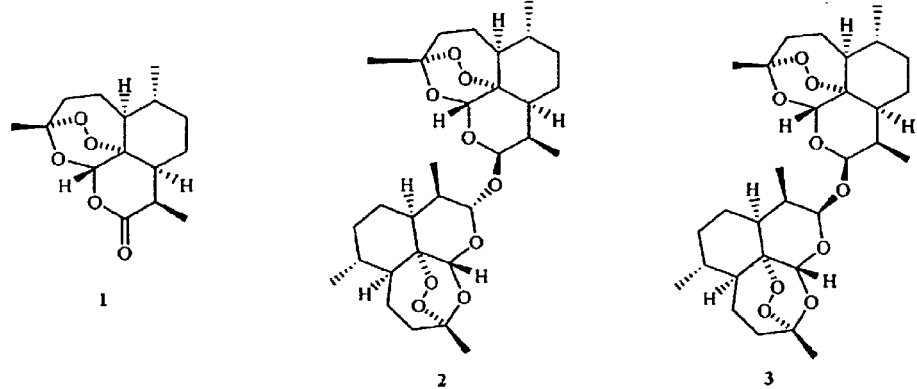
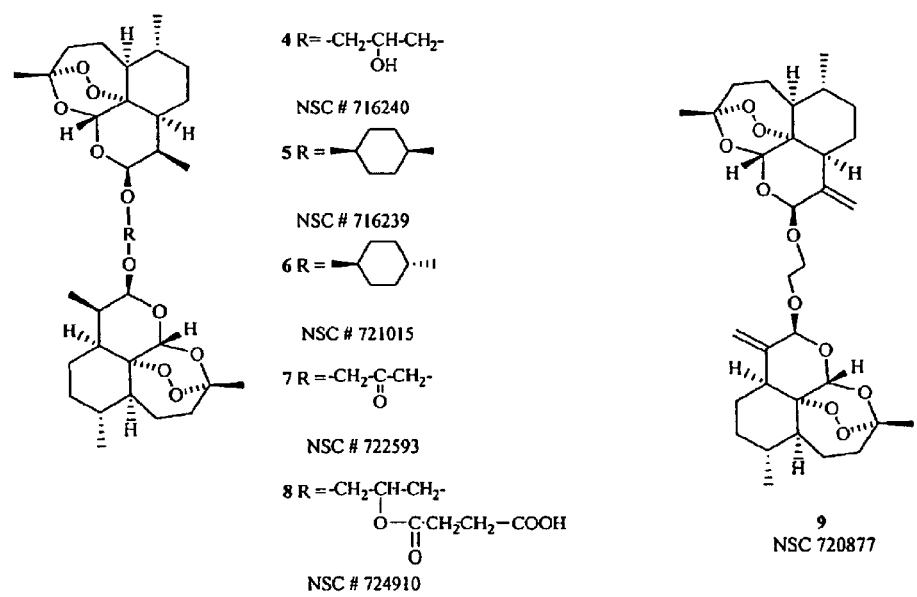

Table 1. Results of *in vitro* anti-cancer testing of compounds 4-9

| Compound | 4 | 5 | 6 | 7 | 8 | 9 |
|---|---|---|---|---|---|---|
| NSC # | 716240 | 716239 | 721015 | 722593 | 724910 | 720877 |
| Panel / Cell Line | | | | | | |
| Leukemia | | | | | | |
| CCRF-CEM | 0.104 | <0.005 | <0.01 | | <0.01 | 0.098 |
| HL-60 (TB) | 0.062 | 0.017 | 0.032 | 0.01 | <0.01 | 0.098 |
| K-562 | 0.06 | 0.014 | 0.041 | 0.01 | <-/01 | 0.050 |
| MOLT-4 | 0.298 | 0.02 | 0.1 | 0.01 | 0.98 | 0.120 |
| RPMI-8226 | 0.024 | <0.005 | <0.01 | 0.01 | | 0.013 |
| SR | 0.178 | 0.014 | 0.306 | 0.01 | | 0.028 |
| Non-Small Cell Lung Cancer | | | | | | |
| A549/ATCC | 0.505 | 0.02 | 0.0188 | <0.01 | 13.6 | 5.370 |
| EKVX | 0.307 | 0.024 | 0.0277 | | 19.5 | 0.479 |
| HOP-62 | 13.3 | 12.3 | | 11.5 | 11.3 | 6.918 |
| HOP-92 | 0.384 | 0.017 | | 0.18 | 0.08 | 0.741 |
| NCI-H226 | 61.7 | 0.347 | 0.0247 | <0.01 | 18.1 | |
| NCI-H23 | 0.135 | 0.022 | 0.0247 | 0.01 | <0.01 | 1.072 |
| NCI-H322M | 62.5 | 16.6 | 0.67 | 8.42 | 10.3 | 11.220 |
| NCI-H460 | ----- | 0.017 | 0.028 | <0.01 | <0.01 | 5.495 |
| NCI-H522 | 0.52 | 0.021 | 0.036 | 0.01 | | 0.398 |
| Colon Cancer | | | | | | |
| COLO 205 | 0.04 | 0.007 | <0.01 | 0.01 | | 0.123 |
| HCC-2998 | 7.02 | 0.018 | 0.018 | | | 6.026 |
| HCT-116 | 0.049 | 0.016 | <0.01 | 0.01 | <0.01 | 0.027 |
| HCT-15 | 0.027 | 0.014 | <0.01 | 0.01 | <0.01 | 0.012 |
| HT29 | 0.268 | 0.026 | 0.011 | 0.01 | <0.01 | 0.043 |
| KM12 | 0.166 | 0.012 | 0.011 | 0.01 | <0.01 | 0.093 |
| SW-620 | 0.099 | 0.012 | 0.024 | 0.01 | | 0.062 |
| CNS Cancer | | | | | | |
| SF-268 | 13.7 | 0.034 | 0.11 | 11.1 | <0.01 | 6.310 |
| SF-295 | 9.52 | 0.028 | 0.061 | 2.93 | | 7.586 |
| SF-539 | 8.64 | 0.02 | 0.092 | | 8.3 | 5.370 |
| SNB-19 | 27.6 | 0.099 | 0.37 | 0.0213 | | 10.965 |
| SNB-75 | 8.25 | 0.03 | 0.2 | 6.01 | 11.7 | |
| U251 | ----- | 0.019 | 0.016 | <0.01 | <0.01 | 0.288 |

Fig. 2A

Table 1, Contd
GI50 (uM)

| Compound | 4 | 5 | 6 | 7 | 8 | 9 |
|---|---|---|---|---|---|---|
| NSC # | 716240 | 716239 | 721015 | 722593 | 724910 | 720877 |
| Panel / Cell Line | | | | | | |
| Melanoma | | | | | | |
| LOXIMVI | 0.11 | 0.017 | 0.013 | 0.01 | | |
| MALME-3M | 14.9 | 0.027 | 0.06 | 0.01 | <0.01 | 0.204 |
| M14 | 8.82 | 0.044 | 0.07 | 0.01 | 4.05 | 7.244 |
| SK-MEL-2 | 14.2 | 0.024 | 0.3 | 0.031 | 3.42 | 3.162 |
| SK-MEL-28 | 9.39 | 0.085 | 98.8 | 11.7 | 15.5 | 6.026 |
| SK-MEL-5 | | | 0.49 | <0.010 | | 0.501 |
| UACC-257 | 0.257 | 0.027 | 0.074 | <0.010 | 11.0 | 0.479 |
| UACC-62 | 0.296 | 0.022 | 0.045 | <0.010 | | 7.244 |
| Ovarian Cancer | | | | | | |
| IGROVI | 13.1 | 6.75 | 0.055 | 1.74 | 14.3 | 0.617 |
| OVCAR-3 | 0.171 | 0.015 | 0.067 | <0.010 | | 0.107 |
| OVCAR-4 | 0.209 | 0.024 | 0.053 | 0.069 | | 0.072 |
| OVCAR-5 | 17.7 | 0.152 | 0.042 | <0.010 | 0.01 | 5.012 |
| OVCAR-8 | 0.252 | 0.019 | 0.057 | <0.010 | 17.7 | 0.372 |
| SK-OV-3 | 21.4 | 0.034 | 0.166 | | | 10.965 |
| Renal Cancer | | | | | | |
| 786-0 | ----- | 0.031 | 0.027 | <0.010 | <0.01 | 0.347 |
| A498 | 15.8 | 0.04 | 0.37 | 14.3 | | 50.119 |
| ACHN | ----- | 0.027 | 0.042 | <0.010 | | 6.310 |
| CAKI-1 | 0.458 | 0.037 | 0.33 | 0,025 | 0.01 | 1.778 |
| RXF 393 | 0.213 | 0.018 | 0.29 | 15.4 | <0.01 | 6.457 |
| SN12C | 0.303 | 0.025 | 0.097 | <0.010 | 8.82 | 7.244 |
| TK-10 | 14.1 | 0.029 | 0.12 | <0.010 | <0.01 | 0.219 |
| UO-31 | 0.127 | 0.018 | 0.12 | <0.010 | 6.95 | 0.182 |
| Prostate Cancer | | | | | | |
| PC-3 | 0.0354 | 0.0105 | <0.01 | <0.010 | <0.01 | 0.063 |
| DU-145 | 13.8 | 0.028 | 0.34 | 11.2 | | 7.586 |
| Breast Cancer | | | | | | |
| MCF7 | 0.095 | 0.0158 | 0.042 | <0.010 | <0.01 | 0.148 |
| NCI/ADR-RES | 0.34 | 0.077 | 0.13 | <0.010 | 0.29 | 0.537 |
| MDA-MB-231/ATCC | 45.8 | 0.092 | 0.52 | <0.010 | 0.01 | 13.183 |
| HS 578T | 12.5 | 0.049 | 0.52 | | 17.5 | 0.074 |
| MDA-MB-435 | ----- | 0.028 | 0.07 | <0.010 | <0.01 | 0.447 |
| MDA-N | 0.368 | 0.024 | 0.077 | | | 0.513 |
| BT-549 | 0.408 | 0.042 | | 0.05 | 19.4 | 7.586 |
| T-47D | 0.027 | <0.005 | <0.01 | <0.010 | | 0.014 |

Fig. 2B

Table 2. Results of *in vitro* anti-cancer testing of compounds 4-9
TGI (u M)

| Compound | 4 | 5 | 6 | 7 | 8 | 9 |
|---|---|---|---|---|---|---|
| NSC # | 716240 | 716239 | 715015 | 722593 | 724910 | 720877 |
| Panel / Cell Line | | | | | | |
| Leukemia | | | | | | |
| CCRF-CEM | 18.3 | 8.32 | >100 | <0.01 | >100 | 8.318 |
| HL-60 (TB) | 0.18 | 0.03 | 0.44 | 12.4 | | 12.882 |
| K-562 | >62.5 | 7.67 | >100 | 12.1 | >100 | 1.122 |
| MOLT-4 | >62.5 | 9.24 | >100 | <0.01 | >100 | 11.220 |
| RPMI-8226 | 11.2 | 0.276 | 0.024 | <0.01 | | 0.234 |
| SR | 6.96 | 0.762 | 58.6 | 4.4 | | 8.318 |
| Non-Small Cell Lung Cancer | | | | | | |
| A549/ATCC | 19.3 | >50 | >100 | 17.4 | 57.6 | 16.218 |
| EKVX | >62.5 | 15.4 | | | 72.4 | 9.772 |
| HOP-62 | >62.5 | >50 | | .24.0 | 26.0 | 14.454 |
| HOP-92 | 42.2 | ---- | | 22.9 | 21.2 | 13.490 |
| NCI-H226 | >62.5 | 27 | 38.9 | 14.8 | 35.0 | |
| NCI-H23 | >62.5 | >50 | >100 | 21.2 | 12.1 | 25.704 |
| NCI-H322M | >62.5 | >50 | >100 | 24.7 | 37.9 | 32.359 |
| NCI-H460 | 27.1 | 26.1 | >100 | 17.0 | 16.5 | 13.490 |
| NCI-H522 | >62.5 | 18.5 | 0.41 | 16.1 | 37.5 | 10.715 |
| Colon cancer | | | | | | |
| COLO 205 | 0.21 | 0.016 | 0.012 | <0.01 | | 0.501 |
| HCC-2998 | 19.3 | 8.86 | | | | 13.183 |
| HCT-116 | >62.5 | 8.3 | 0.042 | 14.2 | 15.6 | 8.710 |
| HCT-15 | >62.5 | >50 | 0.054 | <0.01 | 10.3 | 7.413 |
| HT29 | >62.5 | >50 | >100 | 20.3 | >100 | 8.913 |
| KM12 | >62.5 | 18.6 | >100 | 12.5 | <0.01 | 12.303 |
| SW-620 | 13.4 | >50 | >100 | 16.3 | | 21.878 |
| CNS Cancer | | | | | | |
| SF-268 | >62.5 | >50 | >100 | 36.6 | 20.7 | 17.378 |
| SF-295 | >62.5 | >50 | >100 | 20.9 | | 21.878 |
| SF-539 | 19.1 | 13.8 | >100 | 25.3 | 38.6 | 11.482 |
| SNB-19 | >62.5 | >50 | >100 | 18 | | 50.119 |
| SNB-75 | >62.5 | 42 | >100 | 39.2 | 35.3 | |
| U251 | 49.2 | >50 | >100 | 17.7 | 20.2 | 11.749 |

Fig. 3A

Table 2, cont

| TGI (uM) Compound | 4 | 5 | 6 | 7 | 8 | 9 |
|---|---|---|---|---|---|---|
| NSC # | 716240 | 716239 | 721015 | 722593 | 724910 | 720877 |
| Panel / Cell Line | | | | | | |
| Melanoma | | | | | | |
| LOXIMVI | 2.77 | 2.25 | 0.099 | <0.01 | | |
| MALME-3M | >62.5 | >50 | >100 | 12.8 | 10.4 | 14.791 |
| M14 | >62.5 | >50 | >70.6 | 15.3 | 26.9 | 16.218 |
| SK-MEL-2 | >62.5 | 26.2 | 2.51 | 18.6 | >100 | 17.783 |
| SK-MEL-28 | >62.5 | >50 | >100 | 28.7 | >100 | 13.490 |
| SK-MEL-5 | >62.5 | 0.56 | 12.7 | 15.6 | | 21.380 |
| UACC-257 | >62.5 | 21.7 | >100 | 13.6 | 53.2 | 22.909 |
| UACC-62 | >62.5 | 11.9 | >100 | 14.8 | | 14.791 |
| Ovarian Cancer | | | | | | |
| IGROVI | >62.5 | >50 | 27.4 | 7.59 | >100 | 2.951 |
| OVCAR-3 | 20.1 | 6.15 | 3.3 | 17.4 | | 10.233 |
| OVCAR-4 | >62.5 | >50 | >100 | 27.4 | | 1.288 |
| OVCAR-5 | >62.5 | >50 | >100 | 24.2 | 13.4 | 14.454 |
| OVCAR-8 | >62.5 | >50 | 0.242 | 0.128 | 63.5 | 11.220 |
| SK-OV-3 | >62.5 | >50 | >100 | 23.5 | | 37.154 |
| Renal Cancer | | | | | | |
| 786-0 | 16.5 | >50 | 0.452 | 15 | 18.5 | 9.333 |
| A498 | >62.5 | >50 | >100 | 30.1 | | 50.119 |
| ACHN | >62.5 | 15.8 | >100 | 11.6 | | 12.589 |
| CAKI-1 | 48.8 | 7.7 | 97.3 | 13.2 | 0.66 | 14.791 |
| RXF393 | 24.8 | 0.44 | >100 | 34.1 | 0.21 | 16.982 |
| SN12C | 16 | 9.37 | >100 | <0.01 | 25.7 | 1.445 |
| TK-10 | >62.5 | >50 | >100 | | 21.2 | 21.878 |
| UO-31 | 1.31 | 0.75 | 25.8 | 1.94 | >100 | 0.912 |
| Prostate Cancer | | | | | | |
| PC-3 | >62.5 | >50 | >100 | 13.2 | 15.2 | 31.623 |
| DU-145 | >62.5 | 23.6 | >100 | 23.3 | | 15.488 |
| MCF7 | 36.8 | 10.8 | >100 | 22.6 | 20.6 | 42.658 |
| NCI/ADR-RES | >62.5 | >50 | >100 | 16.6 | 16.8 | 8.913 |
| MDA-MB-231/ATCC | >62.5 | >50 | >100 | 3.27 | 4.3 | 24.547 |
| HS 578T | >62.5 | >50 | >100 | 19 | 48.5 | 9.333 |
| MDA-MB-435 | >62.5 | 23.9 | >100 | 12.3 | 14.4 | 12.023 |
| MDA-N | >62.5 | >50 | >100 | | | 13.490 |
| BT-549 | >62.5 | >50 | >100 | 22.3 | 40.7 | 26.303 |
| T-47D | >62.5 | 0.038 | 0.091 | <0.01 | | 21.878 |

Fig. 3B

Table 3. Results of *in vitro* anti-cancer testing of compounds 4-9
LC50 (u M)

| Compound | 4 | 5 | 6 | 7 | 8 | 9 |
|---|---|---|---|---|---|---|
| NSC # | 716240 | 716239 | 721015 | 722593 | 724910 | 720877 |
| Panel / Cell Line | | | | | | |
| Leukemia | | | | | | |
| CCRF-CEM | >62.5 | >50.0 | >100 | 19.1 | >100 | 41.687 |
| HL-60 (TB) | 0.55 | 0.17 | >100 | 96.2 | >100 | 50.119 |
| K-562 | >62.5 | >50.0 | >100 | 90.9 | >100 | 32.359 |
| MOLT-4 | >62.5 | >50.0 | >100 | 5.2 | >100 | 45.709 |
| RPMI-8226 | >62.5 | >50.0 | 58.8 | 20.7 | | 26.915 |
| SR | >62.5 | 45.4 | >100 | 33.7 | | 38.019 |
| Non-Small Cell Lung Cancer | | | | | | |
| A549/ATCC | >62.5 | >50.0 | >100 | 54.6 | >100 | 48.978 |
| EKVX | >62.5 | >50.0 | >100 | | >100 | 25.704 |
| HOP-62 | >62.5 | >50.0 | >100 | 50.0 | 59.5 | 29.512 |
| HOP-92 | >62.5 | >50.0 | >100 | 67.7 | 71.0 | 50.119 |
| NCI-H226 | >62.5 | >50.0 | >100 | 51.4 | 67.9 | |
| NCI-H23 | >62.5 | >50.0 | >100 | 66.8 | 37.1 | 50.119 |
| NCI-H322M | >62.5 | >50.0 | >100 | 65.0 | >100 | 50.119 |
| NCI-H460 | >62.5 | >50.0 | >100 | 65.7 | 50.1 | 33.113 |
| NCI-H522 | >62.5 | >50.0 | >100 | 62.1 | >100 | 26.915 |
| Colon cancer | | | | | | |
| COLO 205 | ---- | 0.035 | >100 | <0.01 | | 7.244 |
| HCC-2998 | 53.2 | >50.0 | 72.1 | | | 28.840 |
| HCT-116 | >62.5 | 44.2 | >100 | 45.8 | 40.4 | 21.380 |
| HCT-15 | >62.5 | >50.0 | >100 | 23.1 | 40.2 | 19.953 |
| HT29 | >62.5 | >50.0 | >100 | >100.0 | >100 | 21.380 |
| KM12 | >62.5 | >50.0 | >100 | 43.7 | 13.2 | 36.308 |
| SW-620 | >62.5 | >50.0 | >100 | 44.0 | | 50.119 |
| CNS Cancer | | | | | | |
| SF-268 | >62.5 | >50.0 | >100 | >100.0 | 69.3 | 47.863 |
| SF-295 | >62.5 | >50.0 | >100 | 48.2 | | 50.119 |
| SF-539 | 42.3 | >50.0 | >100 | 55.9 | >100 | 24.547 |
| SNB-19 | >62.5 | >50.0 | >100 | 42.4 | | 50.119 |
| SNB-75 | >62.5 | >50.0 | >100 | >100.0 | >100 | |
| U251 | >62.5 | >50.0 | >100 | 42.1 | 48.1 | 27.542 |

Fig. 4A

Table 3, Cont
LC50 (u M)

| Compound | 4 | 5 | 6 | 7 | 8 | 9 |
|---|---|---|---|---|---|---|
| NSC # | 716240 | 716239 | 721015 | 722593 | 724910 | 720877 |
| Panel / Cell Line | | | | | | |
| Melanoma | | | | | | |
| LOXIMVI | >62.5 | 27.1 | >100 | | | |
| MALME-3M | | | | | 71.1 | |
| M14 | >62.5 | >50 | >100 | 57.0 | 79.5 | 35.481 |
| SK-MEL-2 | >62.5 | >50 | >100 | 73.2 | >100 | 50.119 |
| SK-MEL-28 | >62.5 | >50 | >100 | 70.1 | >100 | 29.512 |
| SK-MEL-5 | >62.5 | 15.6 | >100 | 39.5 | | 50.119 |
| UACC-257 | >62.5 | >50 | >100 | 40.7 | >100 | 50.119 |
| UACC-62 | >62.5 | >50 | >100 | 60/9 | | 30.903 |
| Ovarian Cancer | | | | | | |
| IGROVI | >62.5 | >50 | >100 | 33.7 | >100 | 13.803 |
| OVCAR-3 | >62.5 | 32.5 | >100 | 43.8 | | 36.308 |
| OVCAR-4 | >62.5 | >50 | >100 | >100.0 | | 26.303 |
| OVCAR-5 | >62.5 | >50 | >100 | 74.8 | 48.0 | 40.738 |
| OVCAR-8 | >62.5 | >50 | >100 | 38.8 | >100 | 35.481 |
| SK-OV-3 | >62.5 | >50 | >100 | 55.4 | | 50.119 |
| Renal Cancer | | | | | | |
| 786-0 | 43.2 | >50 | >100 | 39.3 | 55.8 | 22.387 |
| A498 | >62.5 | >50 | >100 | 63.4 | | 50.119 |
| ACHN | >62.5 | >50 | >100 | 34.1 | | 25.119 |
| CAKI-1 | >62.5 | 32 | >100 | 37.4 | 23.2 | 50.119 |
| RXF 393 | >62.5 | 33.6 | >100 | 75.7 | 21.8 | 44.668 |
| SN12C | 47 | >50 | >100 | 28.2 | 68.4 | 28.840 |
| TK-10 | >62.5 | >50 | >100 | 34.4 | >100 | 50.119 |
| UO-31 | 11.3 | 13.8 | >100 | 8.08 | >100 | 2.692 |
| Prostate Cancer | | | | | | |
| PC-3 | >62.5 | >50 | >100 | 63.5 | 79.3 | 50.119 |
| DU-145 | >62.5 | >50 | >100 | 48.5 | | 31.623 |
| Breast Cancer | | | | | | |
| MCF7 | >62.5 | >50 | >100 | >100.0 | >100 | 50.119 |
| NCI/ADR-RES | >62.5 | >50 | >100 | 68.1 | 60.5 | 26.915 |
| MDA-MB-231/ATCC | >62.5 | >50 | >100 | 27.6 | 39.8 | 46.774 |
| HS578T | >62.5 | >50 | >100 | 78.7 | >100 | 50.119 |
| MDA-MB-435 | >62.5 | >50 | >100 | 37.7 | 42.3 | 34.674 |
| MDA-N | >62.5 | >50 | >100 | | | 43.652 |
| BT-549 | >62.5 | >50 | | 57.0 | 85.6 | 50.119 |
| T-47D | >62.5 | >50 | >100 | 36.1 | | 50.119 |

Fig. 4B

Table 4. *In vivo* Hollow Fiber Assay Scores for Compounds 4, 5, and 6

| Compound | NSC Number | IP Score | SC Score | Total Score | Cell Kill |
|---|---|---|---|---|---|
| 4 | 716240 | 12 | 2 | 14 | Y |
| 5 | 716239 | 26 | 10 | 36 | N |
| 6 | 721015 | 18 | 6 | 24 | N |

Fig. 5

Table 5. *In Vitro* Anti-Angiogenesis Activity of Compounds 4, 5, 7 and 8

| Compound | NSC No. | $IC_{50}$ (UM) | | |
|---|---|---|---|---|
| | | Growth Inhibition Assay | Cord Formation | Chemotaxis |
| 4 | 716240 | 0.077 | 30.79 | 1.778 |
| 5 | 716239 | 0.042 | 38.75 | 3.33 |
| 7 | 722593 | 0.057 | >50 | 28.5 |
| 8 | 724910 | 0.056 | 45.8 | 45.3 |
| Control | Taxol | 0.00165 | 0.05 | 0.1 |
| Control | TNP 470 | 0.00316 | 1.00 | 0.5 |

Fig. 6

Table 6. Anti-malarial activity of Compounds 2-6 and 9.

| | P. faciparum (D6 Clone) | | P. faciparum (W2 Clone) | | Cytotoxicity (Vero) |
|---|---|---|---|---|---|
| Compound | IC 50 (ng/mL) | S.i. | IC 50 (ng/mL) | S.i. | TC 50 (ng/mL) |
| Artemisinin (1)* | 6-10 | >24 | 6-10 | >24 | NC |
| 2* | 13 | >37 | 14 | >34 | NC |
| 3* | 6.5 | >73 | 3.8 | >125 | NC |
| 4 | 1.0 | >47.6 | 0.74 | >64.3 | NC |
| 5 | 19 | >25.0 | 13.0 | >37.0 | NC |
| 6 | 24.0 | 19.9 | 30.0 | >15.9 | NC |
| 9 | 11 | >43 | 3.0 | >159 | NC |

*Previously published compounds, included for the purpose of comparison

IC50 = Concentration causing death to 50% of the cells.
S.I. = Selectivity index (IC50 vero cells/IC50 *Plasmodium falciparum*)
TC50 = Concentration toxic to 50% of the cells
NC = Not cytotoxic at highest concentration tested
Highest concentration tested for compounds of this invention = 476 ng/mL.

Fig. 7

Table 7. Anti-malarial Activity of Compounds 4-7

| Compound | Plasmodium falciparum (D6 Clone) | | Plasmodium falciparum (W2 Clone) | | Cytotoxicity (Vero) |
|---|---|---|---|---|---|
| | IC50 (ng/mL) | S.I. | IC50 (ng/mL) | S.I. | TC50 (ng/mL) |
| 4 | 0.2 | >23,800 | 0.74 | >6,430 | >4,760 |
| 5 | 3.0 | >1,590 | 5.2 | >920 | >4,760 |
| 6 | 3.5 | >1,360 | 8.6 | >553 | >4,760 |
| 7 | 0.7 | >7,000 | 0.2 | >23,800 | >4,760 |
| 8 | 1.0 | ND | 1.5 | ND | ND |
| Chloroquine | 9.5 | | >238 | | |
| Artemisinin | 2.8 | | 4.5 | | |

IC50 = Concentration causing death to 50% of the cells.
S.I. = Selectivity index (IC50 vero cells/IC50 Plasmodium falciparum)
TC50 = Concentration toxic to 50% of the cells
Highest concentration tested for compounds of this invention = 4,760 ng/mL.
ND = Not Determined

Fig. 8

Table 8. Anti-Leishmanial Activity of Compounds 4-7

| Compound Number | IC50 (ug/L) | IC90 (ug/mL) |
|---|---|---|
| 4 | 3.1 | 10 |
| 5 | 6.5 | >50 |
| 6 | 5.0 | >50 |
| 7 | 4.8 | 12 |
| Pentamidine | 1.18 | 5 |
| Amphotericin B | 0.08 | 0.14 |

IC50 and IC90 are the compound concentrations that kill 50% and 90% of the cells, respectively, compared to solvent controls.

Highest concentration tested of compounds of this invention = 50 ug/mL.

Fig. 9

DIHYDROARTEMISININ AND DIHYDROARTEMISITENE DIMERS AS ANTI-CANCER AND ANTI-INFECTIVE AGENTS

FIELD OF INVENTION

The present invention relates to dihydroartemisinin and dihydroartemisitene dimers and their use in the treatment of cancer and as antiprotzoal agents.

BACKGROUND OF THE INVENTION

Cancer deaths in the U.S. alone were over 500,000 in 2001, and in spite of many advances, cancer remains one of the leading killers (1). There is a critical need for the development of new anti-cancer agents, especially those with novel and selective mechanisms of action. Although some of the promise of non-cytotoxic therapies is beginning to be realized (e.g. immunostimulants, growth factor antagonists, anti-sense therapy), the mainstay of the treatment of most cancers remains with cytotoxic drugs. In view of the limited success rates, incidence of toxicities, and development of resistance to such agents, there is a dire need for new classes of these drugs, especially those that may act by new mechanisms or exhibit exploitable selectivity. There is also a need for a better understanding of dosing, scheduling, and concomitant therapies in order to optimize treatment protocols.

Natural products have historically been a rich source of new, successful prototype classes of lead compounds from which analogs have been developed. According to a recent review, 60% of the anti-infective and anti-cancer drugs that have successfully advanced to the clinic are derived from natural products (2). Examples of these among currently used anti-cancer agents include the anthracycline class (e.g., doxorubicin), the Catharanthus (Vinca) alkaloids, paclitaxel, and derivatives of podophyllotoxin and camptothecin. A recently published tabulation of natural product-based anti-tumor drugs shows more than 25 agents currently in Phase I or II (3). This and other recent reviews are important reminders of the critical role of natural products as a resource for the discovery of new anti-tumor agents (4,5).

The natural product artemisinin (1) is a sesquiterpene endoperoxide first isolated in 1971 from the Chinese plant *Artemisia annua* (6). The compounds as numbered herein are depicted in FIG. 1. The compound was shown to have anti-malarial activity against both chloroquine-sensitive and chloroquine-resistant strains of *Plasmodium falciparum.*

Because of the importance of the clinical effects of artemisinin in treating malaria, many derivatives were prepared in order to develop the most effective and least toxic anti-malarial agent. Initially, simple derivatives were prepared—e.g., dihydroartemisinin (DHA, in which the lactone carbonyl is reduced resulting in a hemiacetal), artemether (the methyl ether of DHA) and several other ether and ester analogs. The sodium salt of the hemisuccinate ester (sodium artesunate) was one of these derivatives that showed more activity and less toxicity than artemether, the latter being more active than artemisinin itself. Continued interest in the activity of artemisinin and DHA analogs later resulted in the preparation of artemisinin acetal dimers through reaction of dihydroartemisinin with borontrifluoride-etherate.

In addition to its anti-malarial activity, artemisinin had been reported to have cytotoxic effects against EN-2 tumor cells (7), P-388, A549, HT-29, MCF-7, and KB-tumor cells (8). As more analogs were evaluated for anti-tumor activity, it was reported that the unsymmetrical dimer (2) showed strong cytotoxic activity and was more potent than cisplatin (9). The symmetrical dimer (3) also showed pronounced cytotoxic activity (10).

This finding stimulated interest in other types of DHA dimers. Posner et al. (11) prepared dimers linked with a polyethylene glycol spacer (3 units of ethylene glycol), an eight carbon glycol, and a dithio-derivative. The authors also prepared simpler trioxane dimers. Posner et al. also prepared several dimers of DHA where the linking units between the two molecules of dihydroartemisinin were dicarboxylic acids of different types (12). Zhang and Darbie (13,14) also proposed several dihydroartemisinin dimers to be linked via different coupling agents. Some of these artemisinin dimers and some of the simpler trioxanes had anti-malarial effects, anti-cancer activity, and anti-proliferative effects with some compounds being as active as calcitriol in an anti-proliferative assay in murine keratinocytes.

SUMMARY OF THE INVENTION

This invention comprises compositions containing dihydroartemisinin and dihydroartemisitene dimers with activity as anticancer agents and anti-protozal, including anti-malarial and anti-leishmanial properties. This invention also describes methods of preparation of these compositions and methods of use of such compositions for the treatment of cancer, and protozoal infections, including malaria, or leishmaniasis. The compositions of this invention have not been previously described.

The compounds of this invention represent a potential new class of anti-tumor agents, one that has shown promising activity against solid tumors, and with a pattern of selectivity that suggests a possible new mechanism of action.

DESCRIPTION OF THE INVENTION

In the interest of development of new chemotherapeutic agents, artemisinin dimers were prepared in this invention by condensation of DHA with a variety of vicinal and non-vicinal glycols. These dimers have been evaluated in the NCI anti-tumor screening program, and all passed to the 60-cell line screen (4–9). Several of these compounds have been advanced into further testing by the NCI into the Hollow Fiber Assay (HFA) protocol (Compounds 4, 5, and 6). Additional supplies of Compounds 5 and 6 have been recently prepared and provided to the NCI for testing in xenograft tumor models.

Although the mechanism of action of these DHA dimers remains to be determined, some clues regarding possible molecular targets are suggested. Use of the NCI COMPARE analysis revealed that the cell sensitivity profile of these compounds in the 60-cell line assay was similar to platinum compounds. These compounds inhibit cell replication by forming DNA intrastrand cross-links. Correlations on microarray data for the 60 cell lines also indicate that cells most sensitive to these dimers contain lower levels of the mRNAs encoding proteins involved in integrin and hypoxia signaling. Lower levels of expression of these proteins may result in enhanced sensitivity either because these proteins are direct targets, or because their reduced expression reflects a condition within the cell (e.g., redox potential) that augments sensitivity.

Administration of the instant dimers may be by any of the conventional routes of administration, for example, oral, subcutaneous, intraperitoneal, intramuscular, intravenous or rectally. In the preferred embodiment, the compound is administered in combination with a pharmaceutically-acceptable carrier which may be solid or liquid, dependent upon choice and route of administration. Examples of acceptable carriers include, but are not limited to, starch, dextrose, sucrose, lactose, gelatin, agar, stearic acid, magnesium stearate, acacia, and similar carriers. Examples of liquids include saline, water, edible oils, e.g. peanut and corn.

When administered in solid form, the compound and diluent carrier may be in the form of tablets, capsules, powders, lozenges, suppositories prepared by any of the well known methods. When given as a liquid preparation, the mixture of active compound and liquid diluent carrier may be in the form of a suspension administered as such. The compound is administered in a non-toxic dosage concentration sufficient to inhibit the growth and/or destroy cancer or to destroy protozoal organisms such as malaria and leishmania. The actual dosage unit will be determined by the well recognized factors as body weight of the patient and/or severity and type of pathological condition the patient might be suffering with. With these considerations in mind, the dosage unit for a particular patient can be readily determined by the medical practitioner in accordance with the techniques known in the medical arts.

The compounds of this invention have been prepared by reaction of dihydroartemisinin or dihydroartemistene with a variety of optionally substituted 1,2-, 1–3- or 1,4 glycols under acidic conditions (borontrifluoride etherate) in dry ether followed by chromatography of the reaction mixture to isolate the desired product. Optional substitutients include, for example, alkoxy or acyloxy groups. The dimers of the present invention can also be prepared by the reaction of dihydroxy ketones such as, for example, dihydroxyacetone, with DHA or dihydroartemistene followed by reduction of the keto-group and reaction of the hydroxy group formed in the reduction of the ketone with hydroxy reactive compounds such as mono or dicarboxylic acids as their acid halides and acid anhydrides. The starting material (dihydroartemisinin) is prepared by sodium borohydrite reduction of the natural product artemisinin (1). The latter compound is isolated from the leaves of *Artemisia annua* following the procedures previously described (15, 16). The compounds of the invention were tested in the NCI anti-tumor screen and in the anti-malarial and anti-Leishmanial screens. The activities are shown in Tables 1–8 as shown in FIGS. 2A, 2B, 3A, 3B, 4A, 4B and FIGS. 5 to 9.

EXAMPLES

Reactions were run in oven dried round-bottomed flasks. Diethyl ether (ether) was distilled from sodium benzophenone ketyl prior to use under an atmosphere of argon. All chemicals were purchased from Sigma-Aldrich and used without further purification, except the diols, which were dried over grade I alumina prior to use. Artemisinin (I) was isolated from locally grown *Artemisia annua* L. plants, using a literature procedure (15,16), and was reduced to dihydroartemisinin as previously reported (17).

Column chromatography was performed using flash chromatography, using silica gel purchased from Merck (particle size 230–400 mesh). Analytical thin-layer chromatography (TLC) was performed with silica gel 60 $F_{254}$ plates (250 $\mu$m thickness; Merck), using n-hexane-EtOAc mixtures as solvent systems. Visualization was accomplished by spraying with p-anisaldehyde spray reagent followed by heating using a hot-air gun (18).

Mp's were recorded on an Electrothermal 9100 instrument. IR spectra were obtained using AATI Mattson Genesis Series FTIR. Optical rotations were recorded at ambient temperature using JASCO, DIP-370, digital polarimeter. ID and 2D NMR spectra were obtained on Bruker Avance DRX 500 spectrometers at 500 MHz ($^1$H) and 125 MHz ($^{13}$C) or Bruker DRX 400 spectrometer using the solvent peak as the internal standard. HRESIFTMS were obtained using a Bruker Bioapex FT-MS in ESI mode. Low resolution MS were measured on a ThermoQuest aQa LC/MS.

Preparation of the 1,3-β,β-Dihyroartemisinin Dimer with Glycerol (Compound 4)

Example 1

To a stirred solution of dihydroartemisinin (160 mg, 0.56 mmol) in a round bottomed flask (50 mL) in dry ether (10 mL), was added dry glycerol (26 mg) and $BF_3.OEt_2$ (267 $\mu$L) using a hypodermic syringe. The mixture was stirred under argon for 70 min. then quenched and worked up as usual to leave a gummy residue (199 mg). Upon crystallization from ether, it yielded 4 (52 mg) as cubic crystals, 28.7%); $[\alpha]_D$+173° (c 0.022, $CHCl_3$); IR (film) $\nu_{max}$: 3525 (OH), 2953, 2933, 2881, 1449, 1376, 1194, 1176, 1134, 1107, 1027, 991 cm$^{-1}$; $^1$H NMR ($CDCl_3$, 500 Hz, for one of the two identical monomeric units): δ 5.40 (1H, s, H-5, ), 4.79 (1H, d, J J=3.9, H-12), 4.78 (1H, d, J=3.5 Hz, H-12'), 3.87 (1H, m, H-16, H-16', H-17), 3.49 (1H, dd, J=5.9, 4.3 Hz, H-18), 3.42 (1H, q, J=5.4 Hz, H-18'), 2.63 (1H, m, H-11), 2.34 (1H, ddd, J=14.0, 4.0, 3.9 Hz, H-3), 2.00 (1H, m, H-3'), 1.85 (1H, m, H-2), 1.68 (3H, m, H-2', H-8, H-9), 1.46 (2H, m, H-7, H-8'), 1.39 (3H, s, Me-15), 1.34 (1H, m, H-10), 1.21 (1H, m, H-1), 0.92 (3H, d, J=6.4 Hz, Me-14), 0.90 (3H, d, J=7.4 Hz, Me-13), 0.89 (3H, d, J=7.3 Hz, H-13'), 0.87 (1H, m, H-9'); $^{13}$C NMR ($CDCl_3$, 125 MHz): δ 104.5 (s, C-4), 103.13 (d, C-12), 103.06 (s, C-12'), 88.3 (d, C-5), 81.4 (s, C-6), 70.3 (t, C-16), 70.1 (t, C-18), 70.0 (d, C-17), 52.9 (d, C-1), 44.7 (d, C-7, C-7'), 37.7 (d, C-10), 36.8 (t, C-3), 35.0 (t, C-9), 31.27 (d, C-11), 31.25 (d, C-11'), 26.5 (q, C-15), 25.0 (t, C-2), 25.0 (t, C-8), 20.7 (q, C-14), 13.4 (q, C-13); HRESIFTMS [m/z] 625.3512 [M+H]$^+$ (calcd for $C_{33}H_{53}O_{11}$, 625.3582).

Preferred Procedure for Preparation of Compound 4

Example 2

The preferred method of preparing Compound 4 was to first prepare the ketone precursor through condensation of dihydroxyacetone with dihydroartemisinin in the presence of boron trifluoride-etherate followed by sodium borohydride reduction of the resulting ketone to give Compound 4. This is detailed in the following examples.

Preparation of the β,β-Dihydroartemisinin Dimer with Dihydroxyacetone (Compound 7)

Example 3

Dihydroartemisinin (284 mg, 1 mmol) and 1,3-dihydroxyacetone dimer (45.05 mg, 0.25 mmol) were suspended in diethylether (10 mL). To the mixture (cooled to 5° C. under argon) was then added 35.5 mg $BF_3.Et_2O$ (0.25 mmol, 31 $\mu$L) and the mixture stirred at 5° C. for 20 minutes then at room temperature for 1 hr. Workup as usual gave 319 mg of residue.

The residue was chromatographed on silica gel column (30 g) and eluted with hexane:EtOAC (95:5) with polarity increasing to 80:20. Fractions were collected and pooled according to TLC similarities to give four major fractions. The most polar fraction (140.2 mg) was identified as Compound 7 (converts to Compound 4 upon NaBH$_4$ reduction):

$^1$H-NMR in CDCl$_3$ at 500 MHz: δ 5.44 (2H, s, H-5 & H-5'), 4.805 (2H, d, J=3.39 Hz, H-12 & H-12'), two broad doublets (2H each J=17.59) centered at δ4.46 & 4.285 (H-16 & H-18), 2.665 (2H, m, H-11 & H-11'), 2.355 (2H, ddd, H-3), 2.025 (2H, m, H-3'), 1.88 (2H, m, H-2), 1.81 (4H, m, H-9 & H-9'), 1.675 (2H, m, H-8), 1.475 (4H, H-7, H-7', H-10 & H-10'), 1.41 (6H, s, Me-15 & Me-15'), 1.255 (2H, m, H-1 & H-1'), 0.99–0.95 (12H, Me-14, Me-14', Me-13 & Me-13').

$^{13}$C-NMR in CDCl$_3$ at 124 MHz: δ 204.8 (s, C=0), 104.53 (s, C-4), 102.87 (d, C-12), 88.51 (d, C-5), 81.36 (s, C-6), 72.06 (t, C-16 & C-17), 52.89 (d, C-1), 44.67 (d, C-7), 37.75 (d, C-10), 36.77 (t, C-3), 34.99 (5, C-9), 31.13 (d, C-11), 26.47 (q, C-15), 25.03 (t, C-2), 24.74 (t, C-8), 20.69 (q, C-14), 13.43 (q, C-13).

Example 4

To a suspension of 2.84 g dihydroartemisinin (10 mmol) and 450 mg (2.4 mmol) of 1,3-dihydroxyacetone dimer in ether (100 mL) was added 127 μL of BF$_3$.Et$_2$O (142 mg, 1 mmol) at 5° C. The mixture was stirred at room temperature for 30 minutes, then a second portion (127 μL) of BF$_3$.Et$_2$O was added. A third portion and a fourth portion (254 μL) of BF$_3$.Et$_2$O were added at 15-minute intervals making up a total of 4 mmols. Stirring was continued for 1.5 hr. Workup as usual provided an oily residue which was chromatographed in a manner similar to that described under Example 3 and fractions were combined based on their TLC similarities.

The fractions with R$_f$ values corresponding to the dimer prepared in Example 3 were combined and the solvent evaporated to produce 2.05 g of an oily residue which foamed in vacuum. This material was identical to that prepared under Example 3 (Compound 7)

Example 5

To a suspension of 3.3 g dihydroartemisinin (11.6 mmols) and 522 mg, 2.9 mmols) of 1,3-dihydroxyacetone dimer (0.25 equivalent) in ether (100 mL) was added 0.88 mL of BF$_3$.Et$_2$O (0.986 g, 6.9 mmol, 0.6 equivalent) at 5° C. The mixture was then stirred at room temperature for 3 hr, then worked up as usual to provide an oily residue. The residue was chromatographed over silica gel column (130 g) and eluted with mixtures of hexane-EtOAC ranging from 95:5 to 85:15 to give several fractions which were combined according to TLC similarities. Fractions containing the desired product (identical to that prepared under Example 3) were combined to give 1.628 g of Compound 7.

Preparation of the 1,3-β,β-Dihydroartemisinin Dimer of Glycerol (Compound 4) Starting from Compound 7

Example 6

The ketone intermediate (Compound 7), (1.94 g, 312 mmols) was dissolved in 225 mL of a mixture of THF and water (2:1). The solution was stirred and NBH$_4$ (474 mg, 4 molar equivalent) was then added in portions at room temperature over a 15 minute period. The mixture was then neutralized with 2N HCl. The THF was then evaporated under vacuum. The precipitate was filtered and washed with water and air dried to give 1.8 g (92.5% yield) of Compound 4, identical to that prepared under Example 1).

Example 7

The same procedure described under Example 6 was repeated using 0.778 g of Compound 7 to yield 0.73 g of Compound 4.

Preparation of the β,β-Dihydroartemisinin Dimer with Cyclohexanediol (Compounds 5 and 6)

Example 8

In a round-bottomed flask (100 mL) was introduced dihydroartemisinin (850 mg, 3.0 mmol) and dry ether (25 mL) then the mixture was stirred at room temperature with cyclohexane-1,4-diol (mixture of cis and trans) (170 mg). To the stirred solution, BF$_3$.OEt$_2$ (570 μL) was then added using a hypodermic syringe. The stirring was continued for 80 min., then the reaction was quenched and worked up as usual to leave a gummy residue (1.13 g). The residue was loaded on Si gel column (170 g) and eluted with increasing amounts of EtOAc in n-hexane (15→50%). Fractions of 5 mL were collected and similar fractions were pooled by guidance of TLC to afford Compound 5 (238 mg, oil). Earlier fractions were pooled and re-chromatographed on a silica gel column to yield 6 (70 mg, white amorphous solid).

Compound 5; [α]$_D$+142° (c 0.036, MeOH); IR (film) ν$_{max}$: 2938, 2872, 1448, 1375, 1227, 1194, 1122, 1099, 1029 cm$^{-1}$; $^1$H NMR (CDCl$_3$, 500 MHz, for one of the identical monomereric units): δ 5.42 (1H, s, H-5), 4.90 (1H, d, J=3.3, H-12), 3.78 (1H, brs, H-16), 2.62 (1H, m, H-11), 2.36 (1H, ddd, J=14.0, 12.4, 3.8 Hz, H-3), 2.04 (1H, m, H-3'), 1.88 (2H, m, H-2, H-8), 1.77 (2H, m, H-2', H-8'), 1.71 (2H, m, H-17a, H-17b), 1.65–1.56 (4H, m, H-9, H-9', H-17'a, H-17'b), 1.48 (1H, m, H-7), 1.43 (3H, s, Me-15), 1.32 (1H, m, H-10), 1.25 (1H, m, H-1), 0.95 (3H, d, J=6.2 Hz, Me-14), 0.90 (3H, d, J=7.2 Hz, Me-13); $^{13}$C NMR (CDCl$_3$, 125 MHz): δ 104.4 (s, C-4), 100.0 (d, C-12), 88.4 (d, C-5), 81.5 (s, C-6), 72.7 (d, C-16), 53.0 (d, C-1), 44.9 (d, C-7), 37.9 (d, C-10), 36.9 (t, C-3), 35.2 (t, C-9), 31.2 (d, C-11), 26.6 (q, C-15), 24.9 (t, C-2), 25.1 (t, C-8), 20.7 (q, C-14), 13.5 (q, C-13); HRESIFTMS [m/z] 647.3445[M−1]$^-$ (calcd for C$_{36}$H$_{55}$O$_{10}$, 647.3510).

Compound 6; R$_f$0.42 (n-hexane:EtOAc, 8:2), [α]$_D$+114° (c. 0.042, CHCl$_3$); IR (film) no OH absorption; $^1$H NMR (CDCl$_3$, 400 MHz): δ 5.41 (1H, s, H-5), 4.88 (1H, d, J=3.3 Hz, H-12), 3.75 (1H, brs, H-16), 1.47 (1H, m, H-7), 1.43 (3H, s, Me-15), 1.26 (2H, m, H-1, H-10), 0.95 (3H, d, J=6.0 Hz, Me-14), 0.87 (3H, d, J=7.3 Hz, Me-13); $^{13}$C NMR (CDCl$_3$, 100 MHz): δ 104.4 (s, C-4), 100.4 (d, C-12), 88.4 (d, C-5), 81.6 (s, C-6), 73.9 (t, C-16), 53.0 (d, C-1), 44.9 (m, C-7), 37.9 (d, C-10), 36.9 (t, C-3), 35.1 (t, C-9), 31.2 (d, C-11), 30.4 (t, C-17'), 27.5 (t, C-17), 26.6 (q, C-15), 24.9 (t, C-2), 25.1 (t, C-8), 20.8 (q, C-14), 13.5 (q, C-13); HRESIFTMS [m/z] 671.3772 [M+Na]$^+$(calcd for C$_{36}$H$_{56}$O$_{10}$Na, 671.3765).

Example 9

A mixture of dihydroartemisinin (372 mg 1.31 mmol) and 1,4-cyclohexanediol (cis and trans mixture) (74.4 mg, 0.64 mmol) were suspended in 10 mL dry ether and 0.25 mL of $BF_3.Et_2O$ (280 mg, 1.97 mmol) was added at 0° C. The mixture was then stirred at room temperature for 80 minutes followed by workup by shaking with a sodium bicarbonate solution and separation of the ether layer. The aqueous layer was washed with ether (2×10 mL). The ether layers were combined and washed with water and brine and the ether layer was dried over anhydrous sodium sulfate. Evaporation of the ether resulted in an oily residue (429 mg) which was chromatographed on silica gel column (30 g) and eluted with hexane ether mixtures ranging from 97:3 to 80:20 and fractions were pooled together according to their TLC similarities. Compound 6 (56 mg) was isolated as white solid and Compound 5 (24 mg) was isolated as an oil which foamed under vacuum. These were found to be identical to Compounds 5 and 6 prepared under Example 8.

Example 10

A mixture of dihydroartemisinin (744 mg, 2.62 mmol) and 1,4-cyclohexanediol (149 mg, 1.28 mmol) of the cis and trans mixture were stirred in 20 mL dry ether at 5° C. To the mixture was added $BF_3.Et_2O$ (83 µL, 0.655 mmol) and stirring was continued at room temperature for 1 hr. A second portion of $BF_3.Et_2O$ (83 µL) was added, and the mixture continued to stir for 1 hr. The reaction mixture was then worked up as usual to give 890 mg of an oily residue. Column chromatography of the residue using silica gel (32 g) and elution with hexane:ether 92:2, 96:4, 94:6, and then 90:10 (200 mL each) yielded several fractions pooled according to TLC similarities. Compound 6 was isolated as cubic crystals (238 mg, melting point 146–148° C. Compound 5 was isolated from later fractions as an amorphous foam (184 mg, melting point 93–97° C.). These were found to be identical to those previously prepared under Examples 8 and 9.

Example 11

A mixture of dihydroartemisinin (10 g, 35.2 mmol) and 1,4-cyclohexanediol (cis and trans mixture) (2 g, 17.2 mmol) were suspended in 260 mL dry ether and 1.11 mL of $BF_3.Et_2O$ was added at 0° C. under argon. Two additional portions of $BF_3.Et_2O$ (1.11 mL each) were added after 1 hr intervals. The mixture was then stirred at room temperature for 1 hr after the last addition of $BF_3.Et_2O$ followed by workup as usual to give 12 g of an amorphous residue which was chromatographed on silica gel column to produce 2.69 g of Compound 5 and 2.78 g of Compound 6. These were found to be identical to Compounds 5 and 6 prepared under Examples 8–10.

It must be mentioned that should only Compound 5 or only Compound 6 be desired that only the cis or trans 1,4-Cyclohexanediol be used as the starting material to produce the desired product.

Preparation of the Hemisuccinate Ester of Compound 4 (Compound 8)

Example 12

To a stirred solution of Compound 4 (200 mg, 0.32 mmol) in dry methylene chloride (4 mL) were added triethylamine (0.14 mL, 1.3 equiv), dimethylaminopyridine (16 mg, 0.4 equiv) and succinic anhydride (92 mg, 3 equiv). The resulting solution was slowly stirred at room temperature for 16 hr. Following evaporation of the solvent under reduced pressure, the residue was purified over a silica gel column using hexane:acetone (6:4) as the eluent. The product of the reaction was isolated as white amorphous solid (156 mg) with $R_f$ value of 0.68 (hexane:acetone, 1:1) identified as the hemisuccinate ester of Compound 4 (Compound 8), based on spectral data (see details under Example 13).

Example 13

The reaction of Example 12 was repeated on a larger scale (starting with 550 mg of Compound 4) where all reactants were scaled up proportionally. Purification of the reaction product in the same manner produced 355 mg of Compound 8 as amorphous white powder with the following spectral characteristics:

$^1$H-NMR (acetone-$d_6$, 500 MHz): δ 5.442 (1H, s, H-5), 5.396 (1H, s, H-5'), 5.181 (1H, t, J=4.9 Hz, H-17), 4.755 (1H, d, J=3.4 Hz, H-12), 4.740 (1H, c, J=3.4 Hz, H-12'), 3.990 (2H, m, H-16), 3.608 (1H, dd, J=4.5 Hz & 4.5 Hz, H-18), 3.560 (1H, q, J=5.19 Hz, H-18), 2.652 (4H, m, $CO-CH_2-CH_2-CO-$), 2.548 (2H, m, H-11 & H-11'), 2.304 (2H, ddd, J=3.0, 3.89 & 3.0 Hz, H-3), 2.065 (2H, m, H-3'), 1.886 (2H, m, H-2), 1.786 (2H, m, H-2), 1.786 (2H, m, H-9), 1.686 (2H, m, H-8), 1.534 (2H, m, H-2'), 1.489 (2H, m, H-7 & H-10), 1.332 (6H, s, Me-15 & Me-15'), 1.213 (2H, m, H-1 & H-1'), 0.980–0.937 (12H, Me-14, Me-13, Me-14' & Me-13').

$^{13}$C NMR (acetone-$d_6$, 125 MHz): δ 172.99 (s, CO—OH), 171.7 (s, —CO—O—), 103.9 (s, C-4), 102.46 (d, C-12), 102.32 (d, C-12'), 88.02 (d, C-5), 87.99 (d, C-5'), 80.97 (s, C-6), 71.92 (d, C-17), 66.74 (t, C-16), 66.59 (t, C-18), 53.09 (d, C-1), 44.89 (d, C-7), 37.63 (d, C-10), 36.70 (t, C-3), 34.98 (t, C-8), 31.33 (d, C-11), 31.29 (d, C-11'), 29.48 & 28.78 (t, methylenes of CO—$CH_2$—$CH_2$—CO), 25.72 (q, C-15), 24.98 (t, C-2), 24.7 (t, C-9), 20.23 (q, C-14), 12.81 (q, C-13). HRESIFTMS (m/z) 723.362 [M–H]$^+$, (Calcd. for $C_{37}H_{55}O_{14}$).

Preparation of the β,β-Dihydroartemisitene Dimer with Ethylene Glycol (Compound 9)

Example 14

To a stirred solution of dihydroartemisitene (prepared from artemisinin as previously described (19) (75 mg) in dry ether (15 mL) and ethylene glycol (52 mg), was added $BF_3.OEt_2$ (18 µL) and the reaction mixture was allowed to stand for 24 hr, then quenched and worked up as usual. Column chromatography of the crude reaction mixture using a gradient of EtOAc in n-hexane (20%→50%) afforded Compound 9 as a gum (7 mg), $[α]_D$+181° (c 0.022, MeOH ); IR (film) $ν_{max}$: 2937, 2875, 1681, 1449, 1376, 1191, 1102, 987 cm$^{-1}$; $^1$H NMR (CDCl$_3$, 400 MHz): δ 5.89 (1H, s, H-5), 5.38 (1H, s, H-12), 5.08 (1H, s, H-13a), 4.94 (1H, s, H-13b), 3.89 (1H, d, J=7.5 Hz, H-16a), 3.57 (1H, J=7.6 Hz, H-16b), 2.31 (1H, m, H-7), 1.44 (3H, s, Me-15), 1.25 (2H, m, H-1, H-10), 0.7 (3H, d, J=6.2 Hz, Me-14); $^{13}$C NMR (CDCl$_3$, 100 MHz): δ 143.1 (s, C-11), 114.5 (t, C-13), 103.5 (s, C-4), 101.2 (d, C-12), 88.1 (d, C-5), 80.8 (s, C-6), 66.6 (t, C-16), 51.9 (d, C-1), 48.3 (d, C-7), 37.0 (d, C-10), 36.5 (t, C-3), 34.4 (t, C-9), 31.4 (t, C-8), 24.6 (t, C-2), 25.8 (q, C-15), 20.0 (q, C-13). HRESIFTMS [m/z] 613.2943 [M+Na]$^+$ (calcd for $C_{32}H_{45}O_{10}Na$, 613.2983).

Example 15

Compounds of this invention were subjected to anti-cancer activity screen carried out by the National Cancer Institute (NCI) following their standard protocol against 60 different cancer cell lines. The activity of the compounds of this invention against selected cell lines fro leukemia, non-small cell lung cancer, colon cancer, CNS cancer, melanoma, ovarian cancer, renal cancer, prostate cancer, and breast cancer were determined in terms of GI50 (Table 1), TGI (Table 2), and LC50 (Table 3) concentrations. GI50 is the concentration which inhibits 50% of the growth of the cells, TGI is the concentration causing total growth inhibition, and LC50 is the concentration which kills 50% of the cells.

Example 16

Compounds of this invention were further tested under the NCI's Hollow Fiber Assay Standard Protocol which assesses the in vivo activity. Compounds are considered to have enough activity to progress into further testing if the combined IP and SC sores were ≧20 or if the SC score was ≧8 or if there was a net cell kill of one or more cell lines. Table 4 (FIG. 5) shows the results of the testing of compounds of this inversion in this assay.

Example 17

Compounds of this invention were subjected to in vitro assays to assess their anti-angiogenic activity. These assays are carried out by the NCI according to their standard protocol for HUVEC assays for initial in vitro testing. The three assays are the Growth Inhibition Assay, the Cord Formation Assay, and the Cell Migration Assay. Compounds are considered for further testing if activity is shown in at least one of the above assays. Table 5 (FIG. 6) shows the activity of compounds of this invention in these assays.

Example 18

Compounds of this invention were subjected to anti-protozoal screens at the National Center for Natural Products Research (NCNPR) at the University of Mississippi following standard protocols for assessing anti-malarial and anti-Leishmanial activity. Compounds' activities against these two organisms were compared to the activity of standard medications for each organism.

Table 6 (FIG. 7) shows the activity of compounds of this invention against two strains of the malaria parasite (*Plasmodium falciparum*), one is chloroquine sensitive (D6 clone) and one is chloroquine resistant (W2 clone). The cytotoxicity of the compounds was also assessed using Vero cells. The data show that compounds of this invention are more active than chloroquine or artemisinin as anti-malarial drugs.

Table 7 (FIG. 8) shows the activity of a selected group of compounds of this invention against the malaria parasite. These are from different synthetic lots than those tested in Table 6 (FIG. 7). This confirms the activity of compounds of this invention as anti-malarial agents.

Table 8 (FIG. 9) shows the activity of compounds of this invention against the leishmania parasite with activity comparable to that of pentamidine.

Literature Cited

1. American Cancer Society, Statistics for 2001. (http://www.cancer.org/downloads/STT/F&F2001.pdft)
2. Cragg, G. M., Newman, D. J., Snader, K. M.: Natural products in drug discovery and development. *J. Nat. Prod.*, 60:52–60 (1997).
3. Shu Y. Z.: Recent natural products based drug development: a pharmaceutical industry perspective. *J. Nat. Prod.*, 61:1053–1071 (1998).
4. Cragg, G. M., Newman, D. J., Weiss, R. B.; Coral reefs, forests, and thermal vents: the worldwide exploration of nature for novel antitumor agents. *Seminar Oncol* 24:156–163 (1997).
5. Clark, A. M.: Natural products as a resource for new drugs. *Pharmaceut Res* 13:1133–1141 (1996).
6. Report of the Coordinating Group for Research on the Structure of Qing Hao Su. K'O Hsueh T'Ung Pao 22, 142 (1977); Chem. Abstr. 87, 98788g (1977).
7. Beekman, A. C., Barentsen, A. R. W., Woerdengag, H. J., Van Uden, W., Pras, N., El-Feraly, F. S., and Galal, A. M.; *J. Nat. Prod.*, 60: 325 (1997).
8. Zheng, G. Q,; Cytotoxic terpenoids and flavonoids from Artemisia annua, *Planta Medica*, 60 (1): 54–7 (1994).
9. Woerdenbag, H. J., Moskal, T. A., Pras, N., Malingre, T. M., Kampinga, H. H., Konings, A. W. T., and El-Feraly, F. S., Cytotoxicity of artemisinin-related endoperoxides to Ehrlich ascites tumor cells, *J. Nat. Prod.*, 56: 84a (1993).
10. Beekman, A. C., Woprdenbag, H. J., Kampigna, H. H., and Konings, A. W. T.; Stereochemistry-dependent cytotoxicity of some artemisinin derivatives, *Phytother. Res.*, 10, 140 (1996).
11. Posner, G. H., et al; Trioxane Dimers Have Potent Anti-malarial, Anti-proliferative, and Anti-tumor Activities In Vitro, *Bioorganic and Med. Chem.*, 5:1257–65 (1997).
12. Posner, G. H., Ploypradith, P., Parker, M. H., O'Dowd, H., Woo, S.-H., Northrop, J., Krasavin, M., Dolan, P., Kensler, T. W., Xie, S., and Shapiro, T. A.; Antimalarial, Anti-proliferative, and Anti-tumor Activities of Artemisinin-Derived, Chemically Robust, Trioxane Dimers, *J. Med. Chem.*, 42, 4275–80 (1999).
13. Zhang and Darbie, U.S. Pat. No. 5,677,468 (1997).
14. Zhang and Darbie, U.S. Pat. No. 5,856,351 (1999).
15. ElSohly, H. N., Croom, E. M., El-Feraly, F. S., and El-Sheri, M. M., *J. Nat. Prod.*, 53(6):1560–4 (1990).
16. ElSohly, H. N, and El-Feraly, F. S., U.S. Pat. No. 4,952,603 (1990).
17. Lin, A. J., Klyman, D. L., and Milhous, W. K., J. Med. Chem 30, 2147 (1987).
18. El-Feraly, F. S., and Hufford, C. D., J. Org. Chem, 47, 1527 (1982).
19. El-Feraly, F. S., Ayalp, A., Al-Yahya, M. A., McPhail, D. R. and McPhail, A. T., J. Nat. Prod. 53 (1), 66–71 (1990).

We claim:

1. A method of treating cancer comprising administering to a subject suffering from cancer an effective amount of at least one compound of the formula:

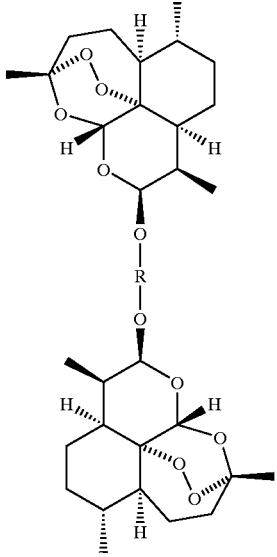

where R is

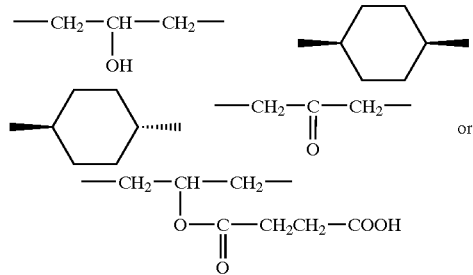

or a compound of the formula:

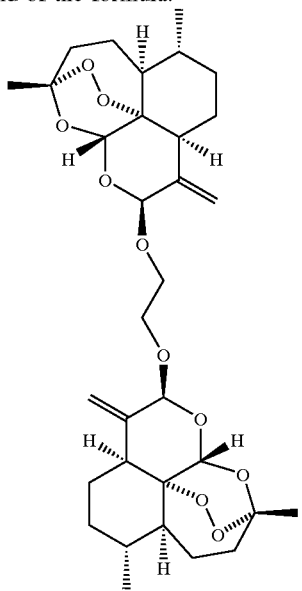

2. A method of treating a protozoal infection comprising administering to a subject suffering from such an infection an effective amount of at least one compound of the formula:

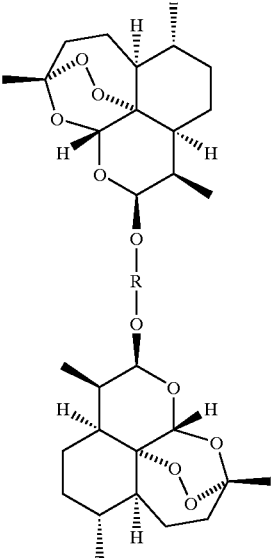

where R is

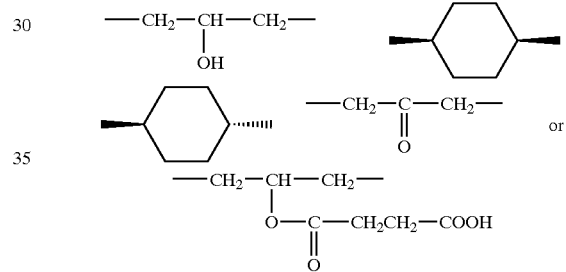

or a compound of the formula:

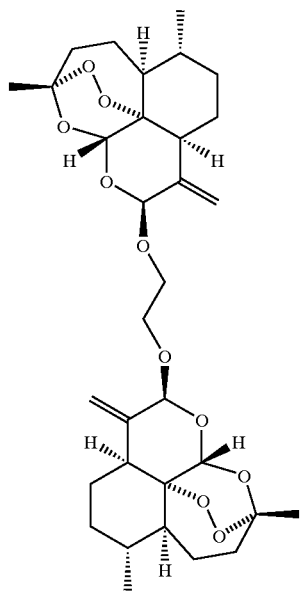

3. A compound of the formula:
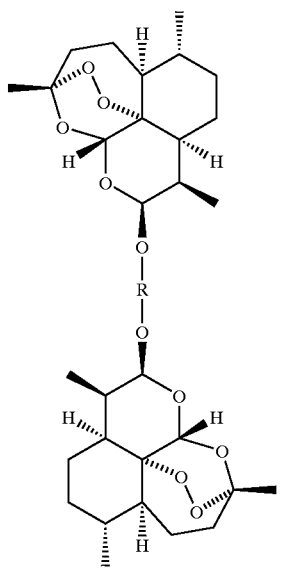
where R is
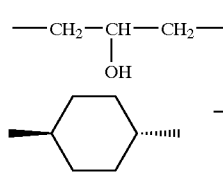
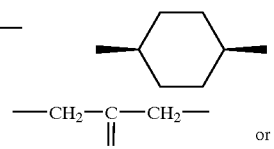
or
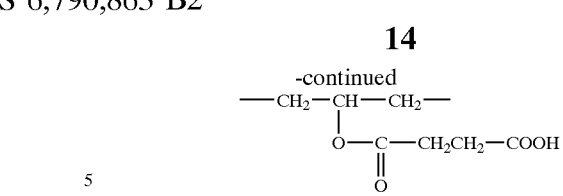
or of the formula:
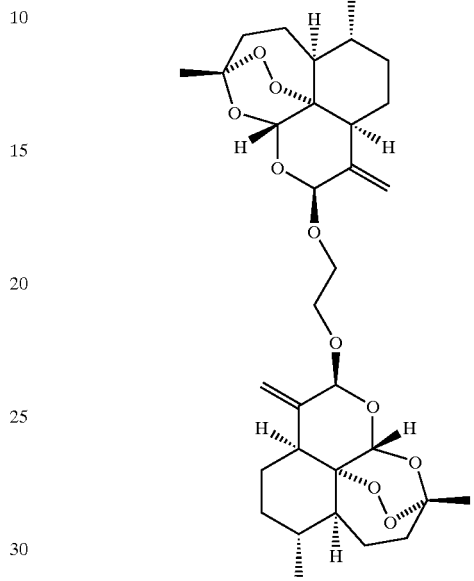
4. A pharmaceutical composition comprising at least of one compound according to claim 3 and pharmaceutically acceptable carrier and/or excipient.
* * * * *